(12) United States Patent
Schmitt

(10) Patent No.: US 9,769,868 B2
(45) Date of Patent: Sep. 19, 2017

(54) MEASUREMENT DEVICE

(71) Applicant: KONINKLIJKE PHILIPS N.V., Eindhoven (NL)

(72) Inventor: Lars Schmitt, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/396,196

(22) PCT Filed: May 27, 2013

(86) PCT No.: PCT/IB2013/054363
§ 371 (c)(1),
(2) Date: Oct. 22, 2014

(87) PCT Pub. No.: WO2013/179204
PCT Pub. Date: Dec. 5, 2013

(65) Prior Publication Data
US 2015/0079908 A1    Mar. 19, 2015

Related U.S. Application Data

(60) Provisional application No. 61/653,440, filed on May 31, 2012.

(51) Int. Cl.
*H04W 76/02* (2009.01)
*H04B 1/50* (2006.01)
(Continued)

(52) U.S. Cl.
CPC ........... *H04W 76/028* (2013.01); *A61B 5/002* (2013.01); *H04Q 9/00* (2013.01); *H04W 4/008* (2013.01); *H04W 52/0216* (2013.01); *H04W 52/0229* (2013.01); *H04Q 2209/88* (2013.01); *H04Q 2209/883* (2013.01); *Y02B 60/50* (2013.01)

(58) Field of Classification Search
CPC ...... H04W 76/028; H04W 4/008; H04B 1/44; H04B 1/50; H04B 7/0693; A61B 2560/0209; A61B 5/002
See application file for complete search history.

(56) References Cited

U.S. PATENT DOCUMENTS 5,805,693 A * 9/1998 Chang .................. H04M 1/271
379/280
7,590,121 B2    9/2009 De Mier
(Continued)

FOREIGN PATENT DOCUMENTS

FR    2758404 A1    7/1998

OTHER PUBLICATIONS

"Health Informatics—Personal Health Device Communication", International Standard, ISO/IEEE 11073-20601, First Edition, May 1, 2010.
(Continued)

*Primary Examiner* — Andrew Wendell

(57) ABSTRACT

A measurement device and communication method for the same is disclosed. The measurement device is adapted to communicate with a monitor device employing a bi-directional communication protocol. The measurement device is adapted to operate in a uni-directional communication mode such that it transmits messages irrespective of response messages transmitted to the measurement device.

14 Claims, 2 Drawing Sheets

(51) Int. Cl.
*A61B 5/00* (2006.01)
*H04Q 9/00* (2006.01)
*H04W 52/02* (2009.01)
*H04W 4/00* (2009.01)

(56) References Cited

U.S. PATENT DOCUMENTS

| | | | | |
|---|---|---|---|---|
| 8,848,912 B2 * | 9/2014 | Takasugi | ............... | H04L 9/3236 380/247 |
| 2008/0269622 A1 * | 10/2008 | Hatlestad | ............... | A61B 5/1116 600/481 |
| 2009/0102681 A1 | 4/2009 | Brennan et al. | | |
| 2009/0271045 A1 * | 10/2009 | Savelle, Jr. | .......... | A01G 25/167 700/284 |
| 2010/0010329 A1 * | 1/2010 | Taub | ................... | A61B 5/0031 600/365 |
| 2010/0014626 A1 | 1/2010 | Fennell et al. | | |
| 2010/0309003 A1 * | 12/2010 | Rousseau | ................. | G07C 1/10 340/573.4 |
| 2011/0184267 A1 * | 7/2011 | Duke | ................. | A61B 5/14532 600/365 |
| 2011/0295335 A1 * | 12/2011 | Sharma | .............. | A61N 1/36007 607/40 |
| 2012/0016305 A1 | 1/2012 | Jollota et al. | | |
| 2014/0112437 A1 * | 4/2014 | Schmitz | ............... | A61B 6/4405 378/62 |

OTHER PUBLICATIONS

Design Differences of a Medical-Grade Foot Switch, Steute's Foot Switch, Setting the Standard for "Medical-Grade" Foot Contorls, Downloaded from www.steuteusa.com/Press/wirelss-foot-contro-desion-considerations whitpaper.asp, Downloaded 2012.
Selecting a Wireless Technology for "Medical-Grade" Foot Controls, .STEUTE, Undated, pp. 1-12, Sep. 24, 2009.

* cited by examiner

MEASUREMENT DEVICE

CROSS-REFERENCE TO PRIOR APPLICATIONS

This application is the U.S. National Phase application under 35 U.S.C. §371 of International Application No. PCT/IB2013/054363, filed on May 27, 2013, which claims the benefit of U.S. Provisional Patent Application No. 61/653,440, filed on May 31, 2012. These applications are hereby incorporated by reference herein.

FIELD OF THE INVENTION

This invention relates to a measurement device, and more particularly to a measurement device for communicating with a monitoring unit.

BACKGROUND OF THE INVENTION

Sensing and measurement devices (such as glucose meters, heart rate monitors, pulse oximeters, pedometers, etc.) are widely used for healthcare and patient monitoring. In order to make monitoring unobtrusive for patients and to maximize patient mobility, measurement devices are increasingly becoming small embedded, battery powered, even body-worn devices. They are also known to employ wireless communications for connecting to a central aggregator or monitoring unit (e.g., a PC, laptop, cell phone, gateway, hub, etc.).

Reduction of power consumption by measurement devices has become an important consideration, and this is mainly due to the small form factor limiting battery capacity.

For reducing the power consumption of the wireless communication tasks, a variety of low-power short-range radio technologies and standards are available (e.g. IEEE 802.15.4, Bluetooth low energy, ANT+, WiFi, etc.). A common principle of all these technologies is to apply duty cycling, i.e. to minimize all unnecessary activity of the radio. For the Medium Access Control (MAC) layer protocol, this essentially translates into the goal to switch on the transmitter only when there is data to be transmitted and to turn on the receiver only when there is data to be received, i.e. to reduce idle listening. In particular the reduction of idle listening is challenging as it is typically not known a priori when data is to be received. Various different MAC level protocols exist which are designed with different strategies to allow efficient medium access with short idle listening periods.

A communication protocol standard of particular relevance in the domain of health and wellness monitoring is the global ISO/IEEE 11073 Personal Health Device (PHD) Communication family of standards. Within that family of standards, ISO/IEEE 11073-20601 defines a generic bi-directional message exchange protocol, which defines communication between a measurement device and monitoring unit through the transmission of messages in both directions (i.e. from the measurement device to the monitoring unit, and from the monitoring unit to the measurement device).

A bidirectional messaging/communication protocol typically comprises the following two categories of messages that are sent from a monitoring unit to a measurement device:

(i) requests from the monitoring unit to the measurement device to send data;

(ii) responses from the monitoring unit to the measurement device (for example to confirm successful reception of data by the monitoring unit).

Such requests and responses cause an increase of idle listening time, as they require the measurement device to activate its receiver to listen for the reception of requests and responses from the monitoring unit.

SUMMARY OF THE INVENTION

According to an aspect of the invention there is provided a measurement device according to the independent claim.

A measurement device according to an embodiment of the invention may operate in a unidirectional messaging mode such that it only transmits messages, irrespective of any response messages that may be transmitted to it.

Embodiments of the invention therefore enable a reduction in the power consumption of a measurement device while maintaining interoperability with a monitoring unit that employs a bidirectional communication protocol (such as ISO/IEEE 11073-20601 for example).

The measurement device may, for example, be a glucose meter, heart rate monitor, pulse oximeter, pedometer, etc. and may be a battery-powered body-worn device that employs a wireless communication method for connecting to a monitoring unit such as a PC, laptop, cell phone, gateway, hub, etc., for example.

In embodiments of the invention, power consumption is reduced by eliminating the need for a monitoring unit to send back data to the measurement device and/or by eliminating the need for a measurement device to use a receiver to listen for the reception of requests and responses from the monitoring unit. A measurement device according to the invention may therefore be operated in a unidirectional (i.e. a 'transmit only') communication mode whilst maintaining interoperability with a monitoring unit that employs a bi-directional communication mode. Such as unidirectional (transmit-only), communication mode makes it possible to switch off a radio receiver in a measurement device (or even negate the need for a radio receiver in the measurement device), thereby reducing power consumption.

BRIEF DESCRIPTION OF THE DRAWINGS

Examples of the invention will now be described in detail with reference to the accompanying drawings, in which.

DETAILED DESCRIPTION OF EMBODIMENTS

Figure 1:
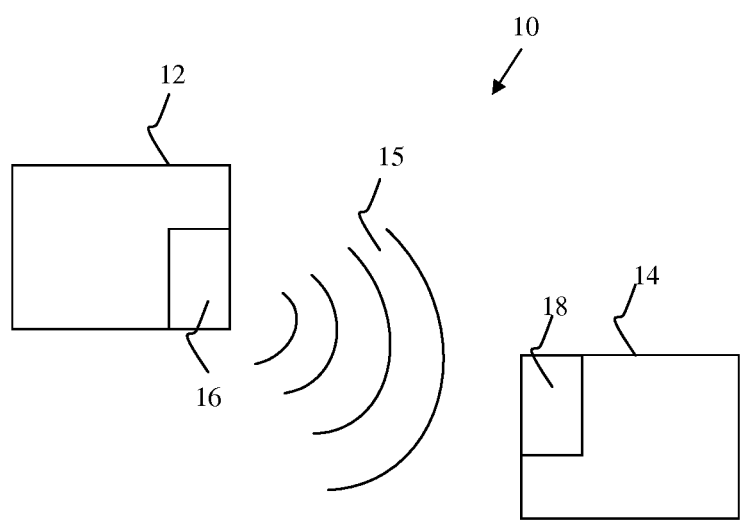
FIG. 1 is a diagram of a measurement system according to an embodiment of the invention.

FIG. 1 shows a measurement system 10 according to an embodiment of the invention. The measurement system comprises a measurement device 12 and a monitoring unit 14, both of which comprise a radio transceiver 16 and 18 respectively. The radio transceivers 16 and 18 are adapted to send and receive messages (i.e. communicate) via a wireless communication link 15

The monitoring unit 14 employs the ISO/IEEE 11073-20601 bi-directional communication protocol for communication. The wireless RF transport is assumed to be of Type 3, as defined within ISO/IEEE 11073-20601. Furthermore, it is assumed that both the measurement device 12 and monitoring unit 14 are paired on the transport level and ready for application layer messaging.

The bi-directional messaging protocol employed by the monitoring unit 14 comprises the following categories of messages that are sent from the monitoring unit to the measurement device:

Category A: Request to send measurement data;

Category B: Request to send measurement data context information;

Category C: Request to change protocol status;

Category D: Request to change device attributes (e.g. control of time, activation of particular actions, etc.);

Category E: Response to confirm successful reception of measurement data sent by the measurement device 12;

Category F: Response to confirm successful reception of context information sent by the measurement device 12; and Category G: Response to a request by the measurement device 12 to change protocol status The above protocol components are a potential source for increasing idle listening time, as they require the measurement unit 14 to activate its receiver to listen for reception of messages.

In the above list, the term context information denotes information that is required by the monitoring unit 14 to correctly interpret raw measurement data sent by the measurement device 12. One example of such context information is a unit of measurement. Typically, context information is rather static and changes much more slowly than measurement data of a physiological parameter. For example, a heart rate sensor typically sends heart rate values in the unit of beats per minute (bpm) during the duration of a connection. Context information is conveyed from the measurement device 12 to the monitoring unit 14 once at the beginning of a connection and thus transmit power consumption is reduced because the context information does not need to be transmitted with each measurement.

Elements of bi-direction communication protocols like those described above for communicating from the monitoring unit back to the measurement device are typically defined for several reasons. Application layer acknowledgements are used to increase the reliability of the overall communication link. Control of attributes of the measurement device can be used, for example, to control the data flow of the communication link by starting or stopping measurement reporting processes. The possibility to request configuration information of the measurement device can be important for regulatory reasons. Bidirectional exchange of protocol status information may be used for keeping the protocol state machines on both sides of the communication link synchronized and to detect if they become unsynchronized, thus increasing the chance for recovery from such a situation.

However, the inventor has realised that a protocol message sent from the monitoring unit 14 to the measurement device 12 can create unwanted power consumption due to the activation of the measurement device's 12 receiver for reception of the protocol message, as well as during idle listening (because the measurement device 12 does not know at what point in time the monitoring unit 14 initiates the transmission of a message).

The inventor has proposed to employ a unidirectional messaging protocol at the measurement device 12 so as to reduce power consumption.

It is noted, however, that in an interoperable system of numerous home health and wellness devices, design of dedicated messaging protocols tailored to the particular needs of an individual device may not be practical. For example, monitoring units typically need to operate with a multitude of different devices and are often manufactured by different manufacturers. The inventor has therefore also realised that there is a need to accommodate for communication with monitoring units that employ conventional bi-directional communication standards such as ISO/IEEE 11073 PHD.

Consequently, in the embodiment of FIG. 1, the transceiver 16 of the measurement device 12 is to operate in a uni-directional communication mode (i.e. a 'transmit only' mode) such that it transmits messages to the monitoring device irrespective of any response messages that may be transmitted to the measurement device 12 from the transceiver 18 of the monitoring unit 14. In this way, the measurement device 12 may circumvent the reception and/or communication of mandatory and optional protocol elements of the bi-directional protocol employed by the measurement unit 12.

Figure 2:
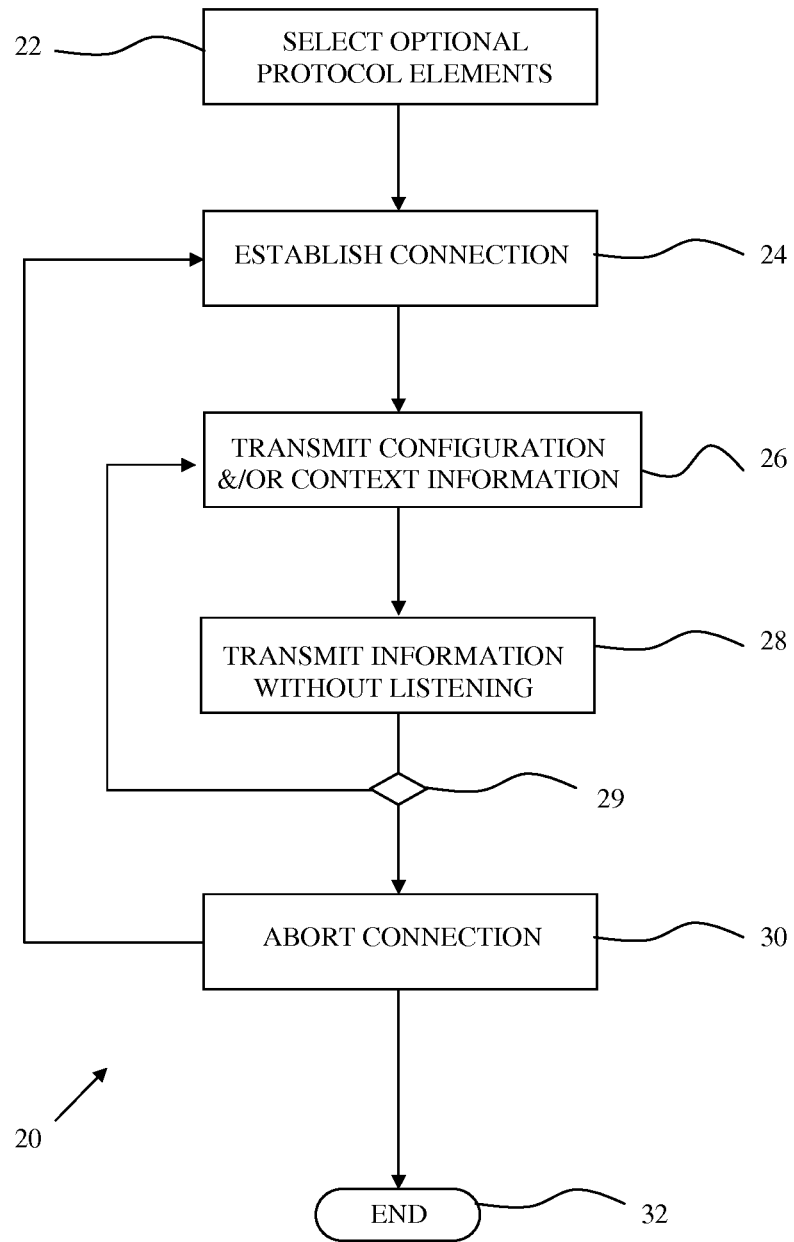
FIG. 2 is a flow diagram of a communication method employed by the embodiment of FIG. 1.

By way of example, a communication session between the measurement device 12 and the monitoring unit 14 will now be described with reference to the flow diagram 20 of FIG. 2.

Firstly, in step 22, the measurement device 12 selects from optional protocol elements those that do not require the feedback of messages from the monitoring unit 14 to the measurement device 12.

Next, on its own initiative, the measurement device 12 establishes a connection with the monitoring unit 14 (step 24). Here, the measurement device 12 opportunistically sends an 'association request' message to the monitoring unit 14 (via the wireless communication link 15), using a 'configuration identifier' that has not been used previously. Based on this, it is a valid assumption that the monitoring unit 14 will not recognize the configuration of the measurement device 12 and that it will reply with an 'association response' message, including a field in the protocol data unit that indicates the acceptance of the 'association request' and another field that indicates that the measurement device configuration is unknown to the monitoring unit. However, the measurement device 12 is adapted to not listen for the 'association response' message, thus avoiding reception of a response from the monitoring unit 14. Furthermore, the measurement device 12 may indicate in the 'association request' message that it is not capable of receiving 'measurement data request' messages from the monitoring unit 14. This can be achieved by setting particular fields in the 'association request' message.

Next, in step 26, the measurement device 12 transmits (via the wireless communication link 15) to the monitoring unit 14 all configuration information and/or context information, as well as all other information relevant for the interpretation of measurement data (step 26). This eliminates the need for the monitoring unit 14 to request this data.

In more detail, the measurement device 12 opportunistically sends a 'configuration report' message to the monitoring unit 14 via the wireless communication link 15. This configuration report message sent by the measurement device 12 contains all configuration information and context information needed by the monitoring unit 14 for later reception of raw measurement data. Assuming that the monitoring device 12 and the measurement unit 14 are interoperable, it is assumed that the monitoring unit 14 will reply with a 'configuration report response' message, including a field in the protocol data unit that indicates the acceptance of the configuration. However, the measurement device 12 is adapted to not listen for a 'configuration report response' message.

The measurement device 12 may also transmit an unconfirmed 'event report' containing all its device attributes, including certification and regulatory information as well as information that time setting capabilities are not supported. This eliminates the need for the monitoring unit 14 to request such data later as well as to send time setting commands. By marking the 'event report' message as unconfirmed, the monitoring unit 14 does not send back a confirmation of successful reception. Thus, reception of a response message at the measurement device 12 is avoided.

The measurement device 12 applies an opportunistic messaging strategy in step 28. In other words, for messages that trigger a response at the monitoring unit 14, a default response is anticipated by the measurement device 12 without actually listening for and receiving such a response from the monitoring unit. In other words, the measurement device 12 determines a potential response from the monitoring unit 14 based on the information it transmits to the monitoring unit 14. One or more subsequent messages transmitted by the measurement device 12 are then based on the assumed response (i.e. the determined potential response). In this way, the measurement device is adapted to operate in a uni-directional communication mode such that it transmits messages irrespective of actual response messages transmitted from the monitoring unit 14 to the measurement device 12.

After transmission of (potentially multiple) information messages in step 28, it may be required to transmit a message with updated configuration and/or context information. Thus, this is checked in step 29, and if it is required to transmit updated configuration and/or context information the method returns to step 26.

After a predetermined amount of time has elapsed, it is determined at step 29 that the communication link is to be aborted. Thus, the measurement device 12 then aborts the communication link with the monitoring unit 14 by sending an 'association abort' message (Step 30). This addresses the possibility that the state machines of measurement device 12 and monitoring unit 14 have become unsynchronized. It is also noted that the step of aborting the communication eliminates the need for the measurement device 12 to listen for potential 'association release' messages or 'association abort' messages that may be sent by the monitoring unit 14.

If further communication with the monitoring unit 14 is required, the measurement device 12 subsequently reinitiates the communication connection (step 24) with the monitoring unit 14 so as to reset the communication link. Steps 24, 26, 28 and 30 can be repeated for continued measurement transmission.

If further communication with the monitoring unit 14 is not required after aborting the connection in step 30, the communication session is ended (Step 32)

It will be appreciated that the embodiment described above avoids protocol messages being sent from the monitoring unit 14 and also relinquished a need to listen for potential protocol messages sent from the monitoring unit 14.

Accordingly, the invention enables a unidirectional transmit-only mode on protocol level. Because the measurement device 12 is adapted to not receive or listen for any messages from the monitoring unit 14, a significant reduction in idle listening time and/or active listening time can be realised. This, in turn, can significantly reduce the power consumption of the measurement device 12, whilst still enabling the measurement device 12 to interoperate with the monitoring unit 14 which utilizes a bidirectional protocol.

In between the transmission of protocol messages, a transmitter unit of the measurement device 12 can enter a sleep mode for further power consumption reduction.

Embodiments of the invention may be suitable for Radio Frequency (RF)-enabled sensing devices having strict power constraints and operating in environments governed by bidirectional communication protocols.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A measurement device adapted to communicate with a monitor device employing a bi-directional communication protocol,
   wherein the measurement device is adapted to operate in a uni-directional communication mode such that it transmits messages via the bi-directional communication protocol to the monitor device irrespective of any response messages transmitted by the monitor device to the measurement device.

2. The measurement device of claim 1, further adapted to determine a potential response from the monitoring unit based on one or more of its transmitted messages, and to transmit one or more subsequent messages based on the determined potential response.

3. The measurement device of claim 1, further adapted to abort and then re-establish communication after a predetermined period of time has elapsed so as to reset a communication link with the monitor device.

4. The measurement device of claim 3, further adapted to modify an identification parameter of the measurement device prior to re-establishing communication.

5. The measurement device of claim 1, wherein the measurement device is a portable electronic device adapted to employ a wireless communication method for transmitting messages.

6. The measurement device of claim 1, wherein the measurement device is adapted to measure a physiological parameter, and wherein a transmitted message comprises information relating to the measured physiological parameter.

7. A measurement system, comprising a measurement device according to claim 1; and the monitoring device employing the bi-direction communication protocol.

8. A communication method for a measurement device to communicate with a monitor device employing a bi-directional communication protocol, the method comprising:
   transmitting messages from the measurement device via the bi-directional communication protocol to the monitor device irrespective of any response messages transmitted by the monitor device to the measurement device so as to operate the measurement device in a uni-directional communication mode.

9. The communication method of claim 8, wherein the step of transmitting messages comprises:

determining a potential response from the monitoring unit based on one or more messages transmitted from the measurement device; and transmitting one or more subsequent messages based on the determined potential response.

10. The communication method of claim 8, further comprising the steps of aborting and then re-establishing communication after a predetermined period of time has elapsed so as to reset a communication link with the monitor device.

11. The communication method of claim 10, further comprising the step of modifying an identification parameter of the measurement device prior to re-establishing communication.

12. The communication method of claim 8, wherein the measurement device is a portable electronic device adapted to employ a wireless communication method for transmitting messages.

13. The communication method of claim 8, wherein the measurement device is adapted to measure a physiological parameter, and wherein a transmitted message comprises information relating to the measured physiological parameter.

14. A computer program embodied on a non-transitory computer readable medium, the computer program comprising computer program codes means adapted to perform all of the steps of claim 8 when said program is run on a computer.

\* \* \* \* \*